(12) United States Patent
Barrilleaux

(10) Patent No.: US 11,478,345 B2
(45) Date of Patent: Oct. 25, 2022

(54) DENTAL NEEDLE VIBRATION DEVICE

(71) Applicant: Leslie A. Barrilleaux, Huntsville, AL (US)

(72) Inventor: Leslie A. Barrilleaux, Huntsville, AL (US)

(*) Notice: Subject to any disclaimer, the term of this patent is extended or adjusted under 35 U.S.C. 154(b) by 384 days.

(21) Appl. No.: 16/831,125

(22) Filed: Mar. 26, 2020

(65) Prior Publication Data

US 2021/0298885 A1 Sep. 30, 2021

(51) Int. Cl.
*A61C 19/08* (2006.01)

(52) U.S. Cl.
CPC .................................... *A61C 19/08* (2013.01)

(58) Field of Classification Search
CPC ...................................................... A61C 19/08
See application file for complete search history.

(56) References Cited

U.S. PATENT DOCUMENTS

| | | |
|---|---|---|
| 5,647,851 A | 7/1997 | Pokras |
| 5,902,279 A * | 5/1999 | Powles ............... A61B 10/0283 604/239 |
| 6,245,091 B1 | 6/2001 | Buncke |
| 6,602,229 B2 * | 8/2003 | Coss ................... A61M 5/3287 604/22 |
| 8,449,482 B2 * | 5/2013 | Blaine ................. A61M 5/422 601/72 |
| 2005/0221253 A1 | 10/2005 | Spinello |

OTHER PUBLICATIONS

Minori Saijo, Emiko Ito, Tatsuya Ichinohe, and Yuzuru Kaneko, Lack of Pain Reduction by a Vibrating Local Anesthetic Attachment, A Pilot Study, American Dental Society of Anesthesiology, Jan. 26, 2005, 62-64, Tokyo Dental College, Chiba, Japan.
Amir Hashem & Shahidi Bonjar, Syringe micro vibrator (SMV) a new device being introduced in dentistry to alleviate pain and anxiety of intraoral injections, and a comparative study with a similar device, Annals of Surgical Innovation and Research, 2011, 5:1, Evin, Tehran, Iran, doi:10.1186/1750-1164-5-1.

* cited by examiner

*Primary Examiner* — John P Lacyk
(74) *Attorney, Agent, or Firm* — Cynthia R. Wright

(57) ABSTRACT

The Dental Needle Vibration Device comprises a vibrator motor device that may be formed onto a disposable dental or surgical needle, or may be reversibly coupled to a self-aspirating syringe. The Dental Needle Vibration Device couples to the disposable dental needle or self-aspirating syringe so that vibration motion from the vibrator motor is transmitted to the needle, improving control over the needle during vibration. The device is formed onto a disposable dental or surgical needle so that it does not rotate about the needle or move along the barrel of the needle. The device is coupled onto a self-aspirating syringe so that it is proximate to the needle in a fixed position so that it does not rotate about the syringe or move along the barrel of the syringe.

5 Claims, 12 Drawing Sheets

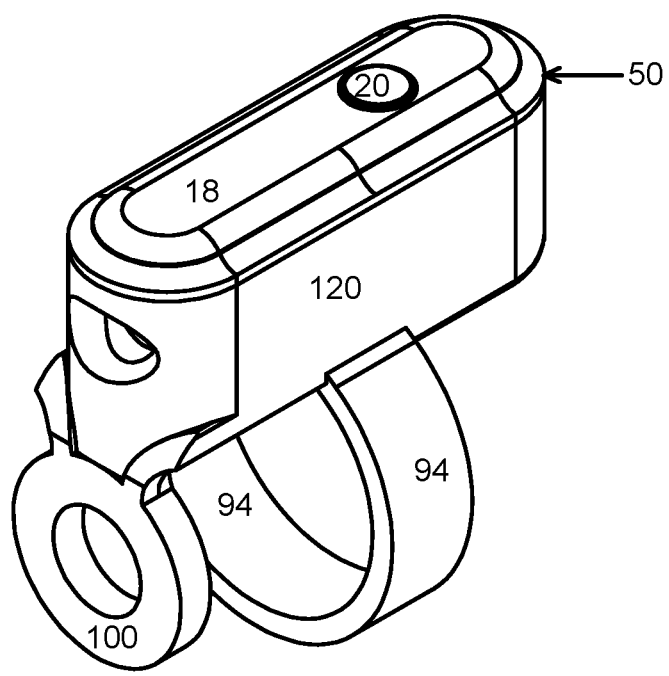
FIG. 12
FIG. 13
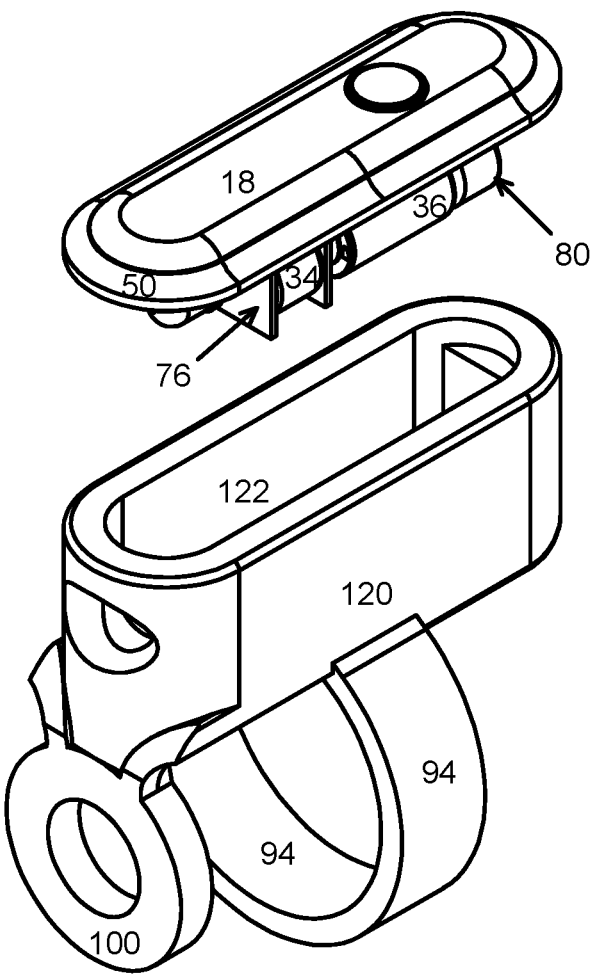

DENTAL NEEDLE VIBRATION DEVICE

CROSS-REFERENCE TO RELATED APPLICATIONS

This application does not claim priority to any patent application.

DISCLOSURE REGARDING PRIOR DISCLOSURES BY THE INVENTOR OR A JOINT INVENTOR

The inventor has not disclosed this invention prior to the filing of this non provisional application.

BACKGROUND OF THE INVENTION

(1) Field of the Invention

Multiple studies have suggested that vibration of a dental needle while a patient is receiving an intraoral injection reduces pain and anxiety. This device comprises a vibrating device that is attached to a dental needle. The device is manipulated so that the dental needle vibrates while a patent is receiving an palatal, mandibular block, intraligamental or a local infiltration injection.

(2) Disclosure of the Prior Art

Dental patients may be plagued with pain phobia. The mention of visiting a dentist can cause severe anxiety and fear in certain individuals. Some studies have shown that vibration can reduce neurological perception of pain. A number of devices are disclosed in the prior art that utilize vibration to reduce pain when a patient is receiving a shot.

Buncke (U.S. Pat. No. 6,245,091 B1) discloses a surgical needle attached to a handle which includes a vibrating device for inducing vibrations in a prescribed frequency range to the needle. The needle's vibration helps avoid damage to major blood vessels and nerves when the needle is pushed through subcutaneous patient tissue. The needle can be utilized while suturing a patient. The device includes a vibratory device within the handle of a surgical needle apparatus. The vibration is transferred to the needle. The vibration is utilized to help avoid damage to major blood vessels and nerves when the needle is pushed through subcutaneous patient tissue. This device produces vibration in the doctor's hand, which can interfere with the doctor's control over the needle making it difficult to perform surgery.

Pokras (U.S. Pat. No. 5,647,851) discloses a vibrating injection device with a vibrating motor disposed in an interior chamber adjacent to a syringe that causes the syringe to vibrate. A plunger drive motor is housed in the interior chamber to expel the contents of the syringe through the needle. A user places an unused needle loaded with anesthetic into the device before use. The device has a motor that provides vibration to the barrel of the syringe, which causes significant vibration in the barrel of the syringe where the user is gripping the device. The device also includes a motorized plunger that pushes onto the plunger of the syringe causing anesthetic to be released from the barrel of the syringe. This device is bulky and difficult to position within a patient's mouth. The device causes anxiety in patients due to it's large size and bulkiness. The dentist user may experience difficulty controlling the amount of anesthesia released from the syringe because a motorized plunger controls the release of the anesthesia. The barrel of the syringe receives vibration, causing vibration in the dentist user's hand reducing the dentist's control over the needle and stimulating the dentist's forearm with vibration. A device that limits vibration in the dentist's forearm is needed while allowing the dentist to maintain control over the needle.

Self-aspirating syringes are a staple for dentists. "Syringe micro vibrator (SMV) a new device being introduced in dentistry to alleviate pain and anxiety of intraoral injections, and a comparative study with a similar device", Shahidi Bonjar *Annals of Surgical Innovation and Research,* 2011, 5:1, http://www.asor-journal.com/content/5/1/1, discloses a micro vibration device that may be reversibly coupled to a standard self-aspirating syringe. The device comprises a stainless steel shell enclosing a vibration motor and four attachment arms that may be secured about the barrel of a self-aspirating syringe. The micro vibrator device equally vibrates the barrel of the syringe and the dentist's hand, causing vibration in the dentist's forearm. Dentists frequently encountering hand and forearm vibration while anesthetizing patients may be subject to increased levels of carpel tunnel syndrome. And, it can be a lot more difficult for a dentist to control the positioning of the needle while the barrel of the syringe is vibrating. The stainless steel attachment arms anchor the device onto the stainless steel barrel. These steel attachment arms may swivel about the barrel causing the device to strike a patient's mouth, increasing the patient's anxiety and causing fear. Additionally, this device protrudes on one side of the barrel forcing the dentist to alter the position of the syringe so that the device does not hit the patient's mouth.

A number of dentists are currently using disposable syringes, such as The Wand® single tooth anesthesia device. The Wand® is disclosed in Spinello (US 2005/0221253 A1). This device is more comfortable to patients than the traditional dental aspirating syringe and enhances control of numbness in collateral tissue. Disposable syringes, such as The Wand®, could benefit from needle vibration which is currently unavailable. The device of Shahidi Bonjar, above, could not be employed with The Wand® because it can not be secured thereon. The metal, autoclavable micro vibrator attachment arms of Shahidi Bonjar would mar into the plastic barrel of the disposable syringe, and would be too large to couple onto the hand piece of the disposable syringe. The micro vibrator would likely rotate about the barrel uncontrollably causing the device to strike the patient's mouth and causing the dentist problems controlling the needle and the flow of anesthesia. This would cause a significant increase in discomfort to the dentist.

BRIEF SUMMARY OF THE INVENTION

This device comprises two embodiments: a one-time use disposable embodiment for use with a disposable syringe, such as The Wand®, and a second, non-disposable embodiment for use with a stainless steel self-aspirating syringe. The disposable embodiment is formed onto the disposable syringe and meant for one-time use. The disposable embodiment is sterilized upon arrival of the device to the dental office. The dentist, or her assistant, simply removes the device from the packaging securing it and it is ready for use. The non-disposable embodiment reversibly couples to the stainless steel self-aspirating syringe, and may be autoclaved between uses. The non-disposable device is formed so that it securely anchors onto the syringe adaptor. Both embodiments secure upon the hand piece or barrel so that the device is fixed and does not rotate or move. Both embodiments direct vibration onto the needle, and away from the hand piece or barrel of the syringe reducing vibration in the dentist's hand and forearm and increasing the dentist's control over the position of the needle during use.

BRIEF DESCRIPTION OF THE DRAWINGS

The invention is described in detail below with reference to the appended drawings.

FIGS. 1 through 16 depict the Dental Needle Vibration Device. In the Figures:

FIG. 1 depicts an angled side and top view of the disposable embodiment of the device.

FIG. 2 depicts an enlarged view of hand piece shown in FIG. 1.

FIG. 3 depicts an exploded view of FIG. 2.

FIG. 4 shows a top angled view of the vibrator motor components of FIG. 3.

FIG. 5 illustrates an angled bottom view of the vibrator motor components of FIG. 3.

FIG. 6 illustrates an exploded view of FIG. 4.

FIG. 7 is a side view of the hand piece of the disposable embodiment of the device.

FIG. 8 depicts an exploded view of FIG. 6.

FIG. 9 is an angled top view of device installed upon a conventional dental anesthesia injection syringe, and FIG. 10 depicts an exploded view of the device shown in FIG. 9.

FIG. 11 illustrates a mid-sectional view of the device installed upon a conventional dental anesthesia injection syringe.

FIG. 12 illustrates a side view of the device.

FIG. 13 illustrates the device of FIG. 12 wherein the vibrating motor components and cover are separated from the device case.

FIG. 14 illustrates an angled top view of the vibrating motor components and cover as depicted in FIG. 13.

FIG. 15 depicts an angled bottom view of FIG. 14.

FIG. 16 depicts an exploded side view of the cap of the vibrating motor components and cover shown in FIG. 14.

DETAILED DESCRIPTION OF THE INVENTION

Figure 1:
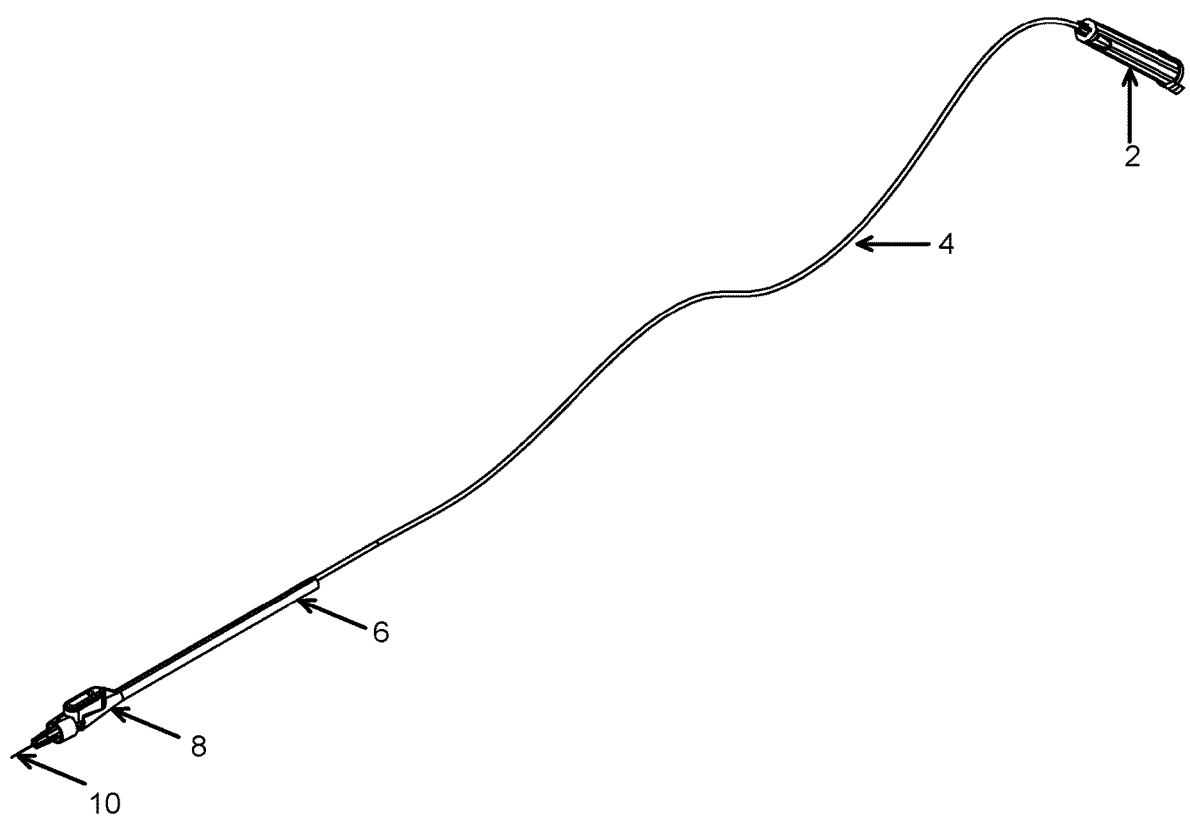

While this invention is susceptible of embodiment in many different forms, there are shown in the drawings and will herein be described in detail, several embodiments with the understanding that the present disclosure should be considered as an exemplification of the principles of the invention and is not intended to limit the invention to the embodiments so illustrated. Further, to the extent that any numerical values or other specifics of materials, etc., are provided herein, they are to be construed as exemplifications of the inventions herein, and the inventions are not to be considered as limited thereto.

The following description and drawings are illustrative and are not to be construed as limiting. Numerous specific details are described to provide a thorough understanding of the disclosure. However, in certain instances, well-known or conventional details are not described in order to avoid obscuring the description. References to one, or an embodiment in the present disclosure, can be, but not necessarily, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same term can be said in more than one way.

Consequently, alternative language and synonyms may be used for any one or more of the terms discussed herein, or is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the disclosure or of any exemplified term. Likewise, the disclosure is not limited to various embodiments given in this specification.

Unless otherwise defined, all technical and scientific terms used herein have the same meaning as commonly understood by one of ordinary skill in the art to which this disclosure pertains. In the case of conflict, the present document, including definitions will control.

Figure 2:
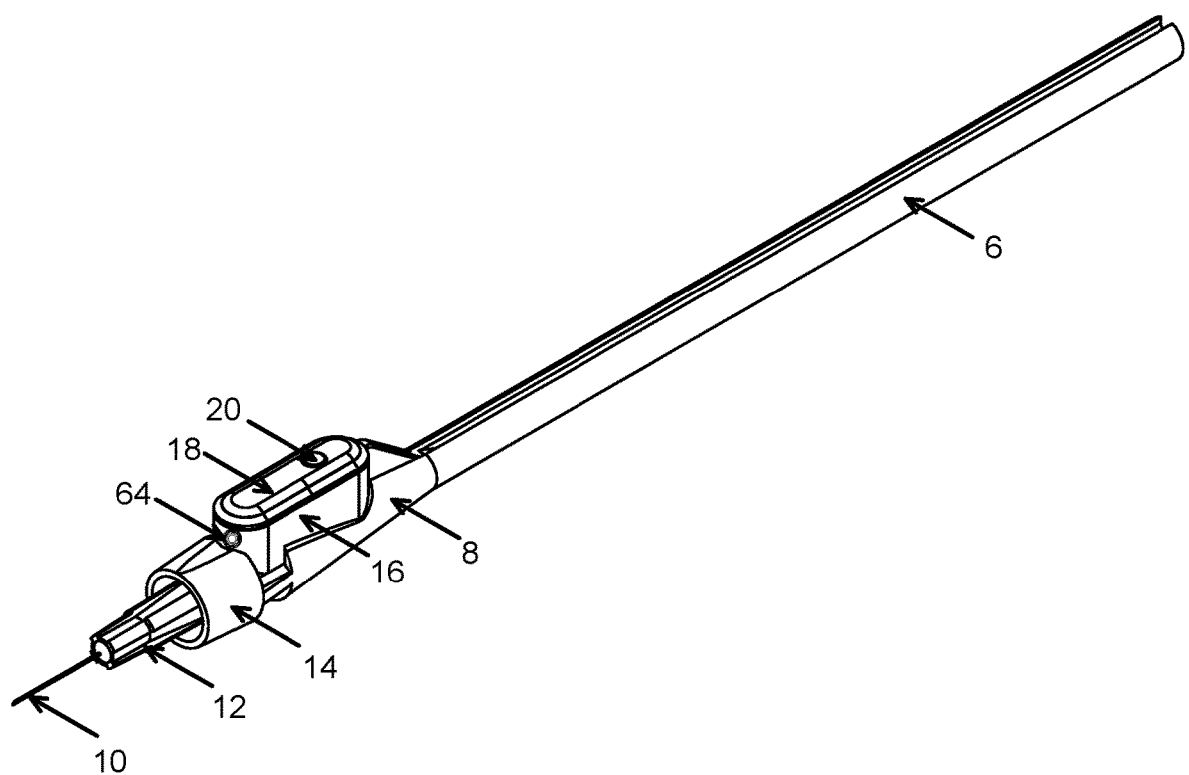

FIGS. 1 through 8 show views of the disposable embodiment of this invention. An angled top and side view is shown in FIG. 1. The disposable syringe may include anesthetic cartridge holder 2, tubing 4 that allows anesthetic to flow from cartridge holder 2 to needle 10, hand piece 6 that facilitates gripping of the device by a dentist or other medical professional, and hand piece base 8. Base 8 is utilized to support the vibrator motor and associated components. The disposable embodiment may be a single tooth anesthetic syringe that is used in dental, surgical, or other medical setting. The hand piece is shown in FIG. 2.

Hand piece 6 connects to hand piece base 8. Adapter 14 couples to needle hub 12. Needle 10 is utilized to penetrate the gums or other tissue. Case 16 encloses the vibrating motor and other components. Case 16 may be formed of plastic or thermoplastic, such as polyamides (nylon), acetal resins, epoxy resins, polystyrene, polycarbonate resins, polyurethane and acrylic thermoplastic, that is strong enough to contain the motor and other components, resistant to water or other solutions, and resistant to microbial growth.

Cover 18 may be permanently affixed to case 16 so that the device is impervious to water and other solutions. Cover 18 may be formed of plastic or thermoplastic, such as polyamides (nylon), acetal resins, epoxy resins, polystyrene, polycarbonate resins, polyurethane and acrylic thermoplastic, that is hardy enough to contain the motor and other components, resistant to water or other solutions, and resistant to microbial growth. On/Off switch 20 allows the dentist or other user to turn the vibrating motor off and on easily and conveniently.

Figure 3:
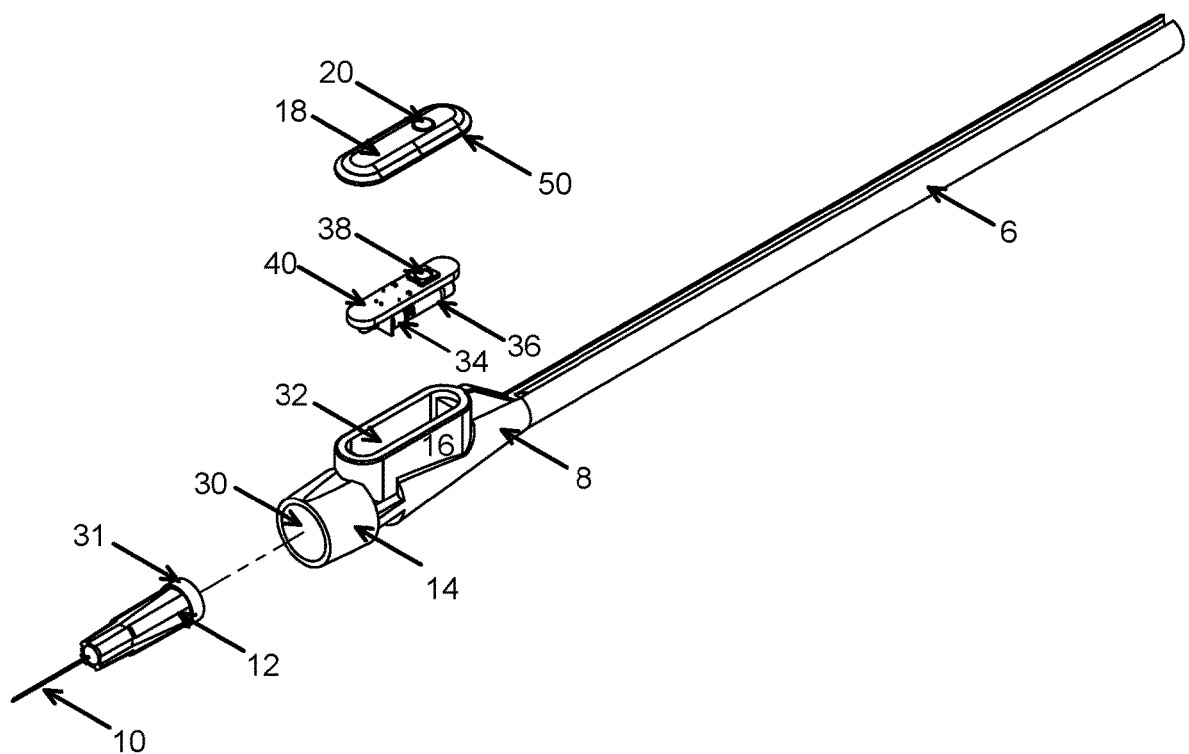

An exploded view of FIG. 2 is shown in FIG. 3. Hand piece 6 is shown connected to hand piece base 8, which is coupled to adaptor 14. Hand piece base 8 forms a secure base for the vibrator motor components preventing any unwanted motion, rotation, or movement of the vibrator motor allowing the dentist or other user to maintain control over needle 10 by focusing the needle vibration onto needle 10, and not hand piece 6. Hilt 30 of needle hub 12 is separated from adaptor 14. Cavity 32 of case 16 is formed to accept vibrator motor components. On/Off switch 20 is seen on cover 18. Sealing edge 50 is not sealed onto case 16. Electronic button 38 is shown on the top surface of printed circuit board (PCB) 40. PCB 40 may be any commonly used printed circuit board available in the market. PCB 40 mechanically supports and electrically connects electrical or electronic components using conductive tracks, pads and other features etched from one or more sheet layers of copper laminated onto and/or between sheet layers of a non-conductive substrate. PCB 40 provides structural support to electronic button 38 and electrically couples electronic button 38 to vibrator motor 36, allowing vibrator motor 36 to be turned On and Off upon physical pressure being applied to electronic button 34 via a user applying physical pressure onto On/Off switch 20 (shown in FIG. 2).

PCB 40 may serve as a support for battery 34 and vibrator motor 36. Battery 34 is shown coupled to PCB 40, and vibrator motor 36 is shown coupled to PCB 40. PCB 40 electrically couples battery 34 to vibrator motor 36. Battery 34 provides power to vibrator motor 36 upon electronic button 38 receiving sufficient pressure. PCB 40 may be programmed so that power is supplied to vibrator motor 36 only while electronic button 38 is receiving physical pressure. Alternatively, PCB 40 may be programmed so that power is supplied to vibrator motor 36 once electronic button 38 receives physical pressure until electronic button 38 receives physical pressure a second time to terminate vibrator motor 36.

Figure 4:
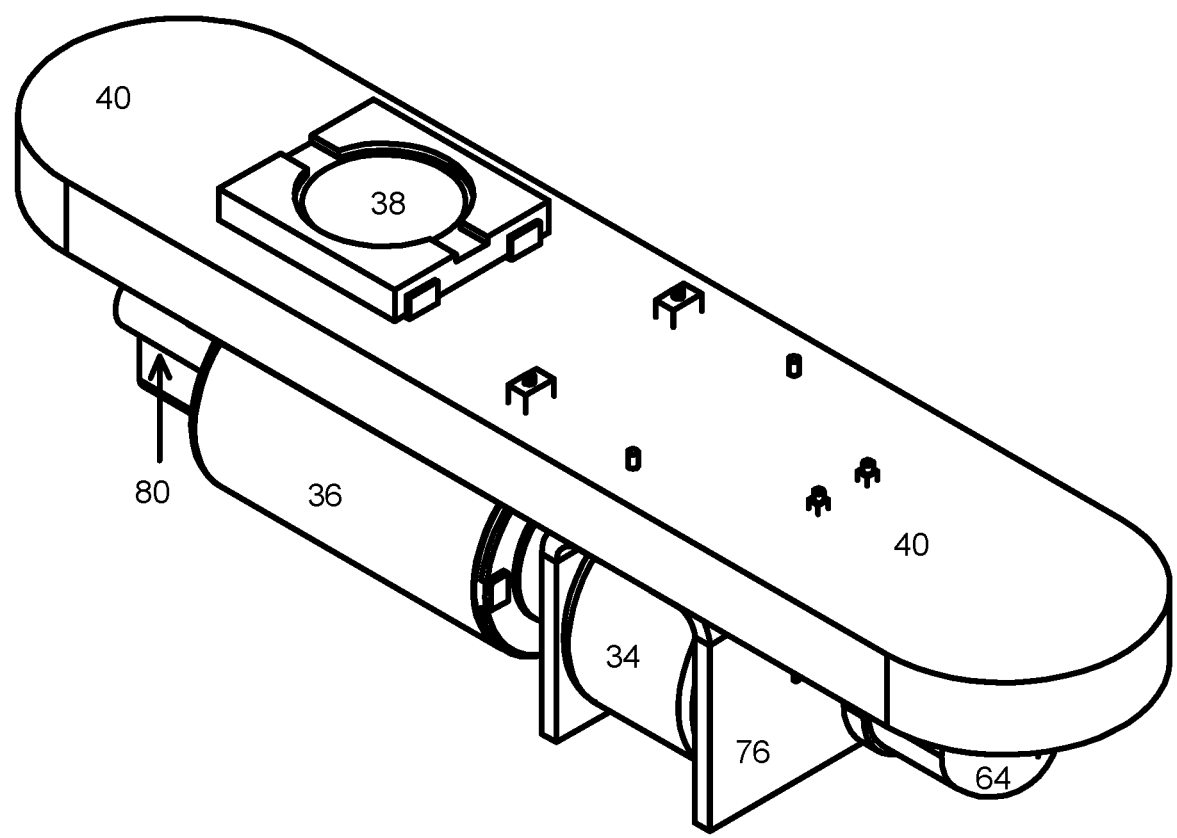

FIG. 4 depicts a top, angled view of the vibrator motor components. The vibrator motor components may comprise: PCB 40, electronic button 38, battery clip 76, battery 34, vibrator motor 36, vibrator motor clip 78 (shown in FIG. 5), weight 80, and optional LED light 64. Battery clip 38 may be composed of metal, and may be formed to secure battery 34 onto PCB 40. Vibrator motor clip 78 may be composed of metal, and may be formed to secure vibrator motor 36 onto PCB 40. Vibrator motor 36 may be a micro mechanical device to generate vibrations. Vibrator motor 36 may comprise an eccentric rotating mass vibration motor (ERM) using a small unbalanced weight or mass on a DC micro motor when it rotates it creates a force that translates to vibration. Weight 80 may be a small, unbalanced weight or mass coupled to the DC micro motor. LED light 64 provides a stream of light that is focused onto the bevel face of needle 10 (needle 10 is shown in FIGS. 1-3).

Figure 5:
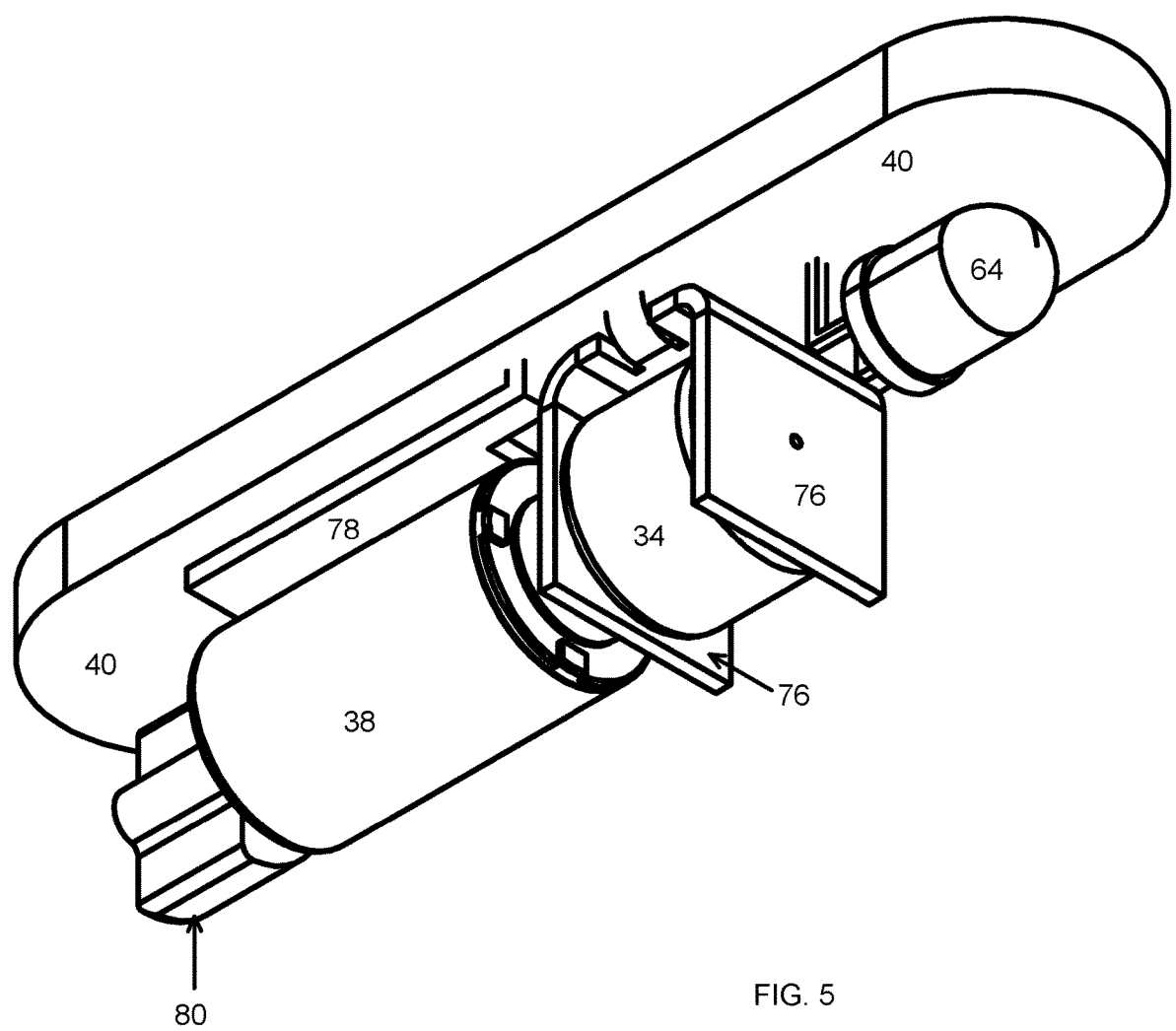
Figure 6:
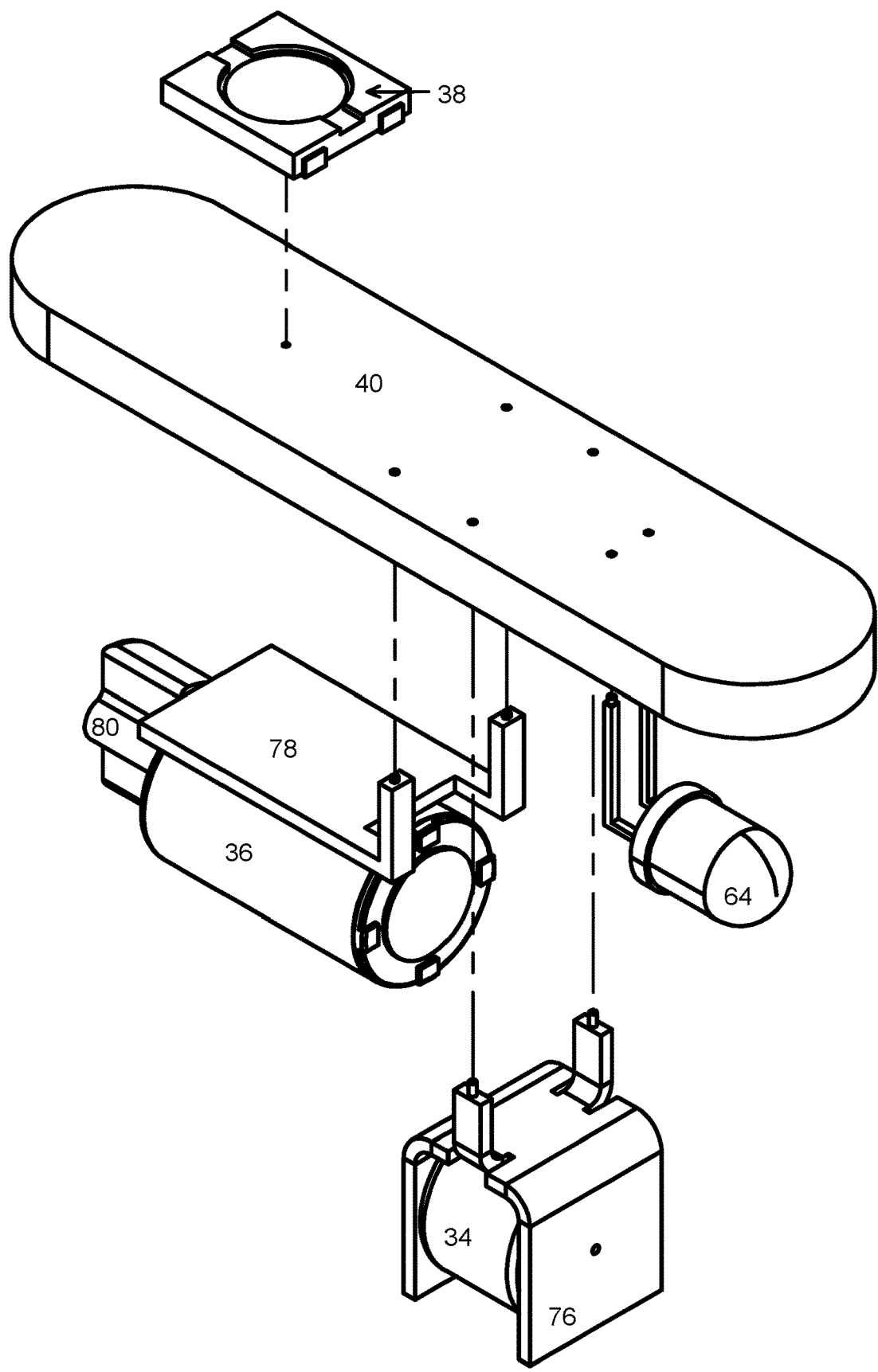

FIG. 5 depicts an angled bottom view of the vibrator motor components. Vibrator motor clip 78 is shown securing vibrator motor 38 to PCB 40. Weight 80 extends from motor 38 and is free to move within cavity 32 of case 16 (shown in FIG. 3). Battery 34 is anchored onto PCB 40 via battery clip 76. LED light 64 is shown wired into PCB 40. FIG. 6 illustrates an exploded view of FIG. 5. Electronic button 38 is shown above PCB 40.

Figure 7:
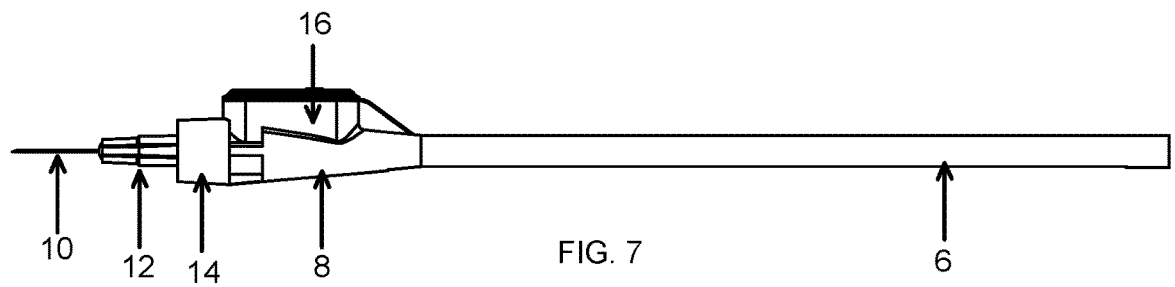
Figure 8:
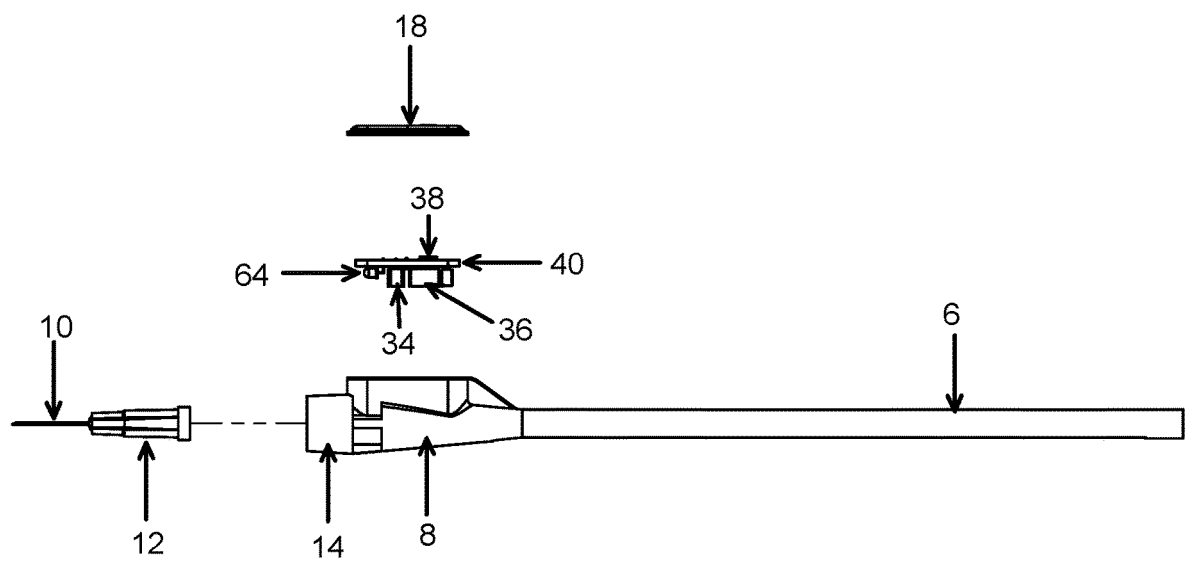

FIG. 7 depicts a side view of the device formed onto hand piece 6, while FIG. 7 depicts and an exploded side view of the disposable device. FIG. 7 depicts case 16 formed onto the disposable device. Hand piece 6 may be designed to bend so that the user can access hard to reach areas of a patient's mouth. Case 6 is formed onto hand piece 6 preventing the device from rotating or moving about the hand piece during use. The positioning of case 6 onto adaptor 14 focuses vibration motion onto need hub 12 and needle 10 reducing vibration in hand piece 6. FIG. 8 depicts the components exploded from hand piece 6. Base 8 supports case 16. LED light 64 is positioned to focus light onto the bevel face of needle 10. Battery 34 provides power for vibrator motor 36, both are secured onto PCB 40. Electronic button 38 controls vibration of needle 10. Cover 18 protects the vibrator motor components from damage due to water or other liquids.

Figure 9:
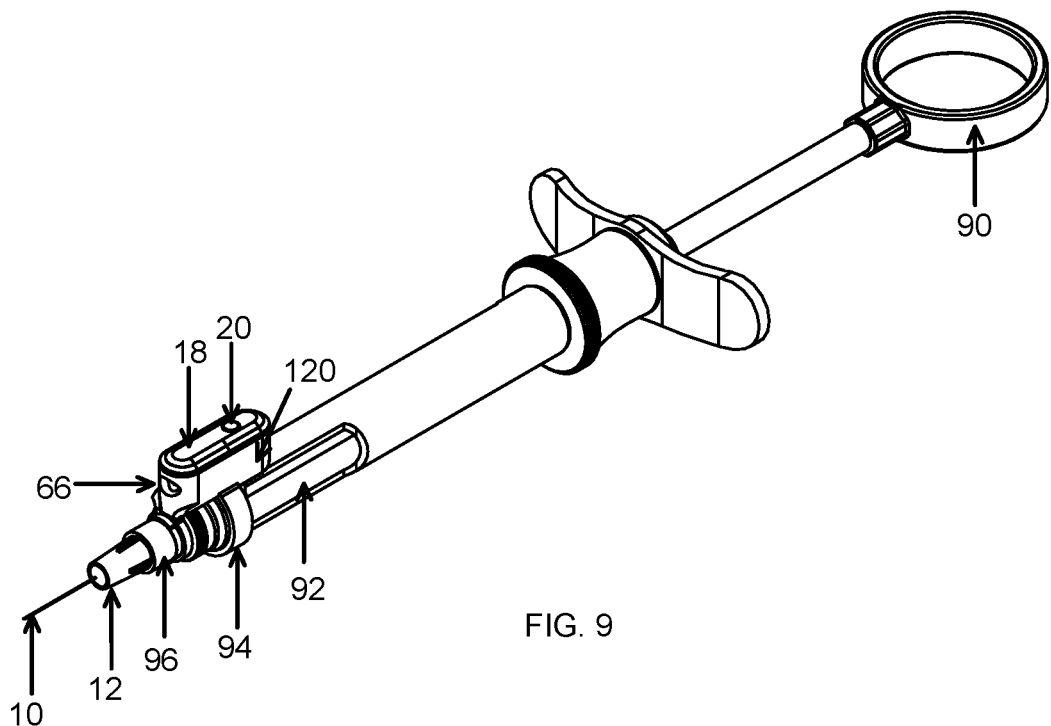
Figure 10:
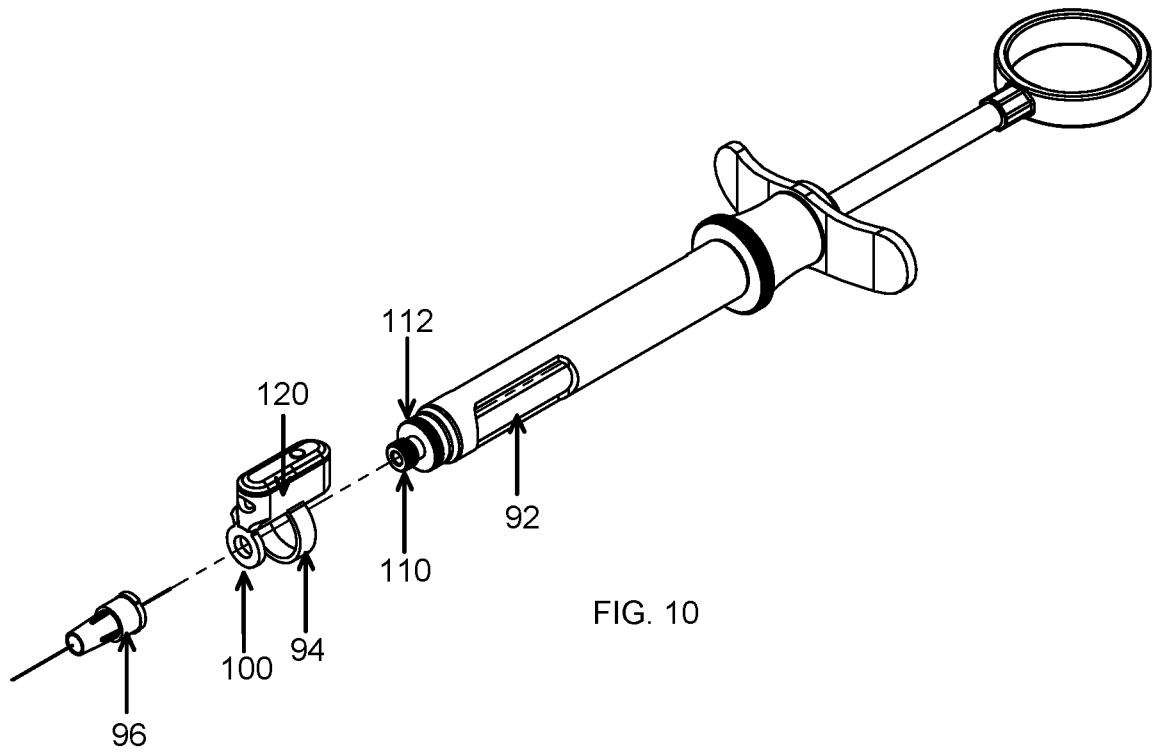
Figure 11:
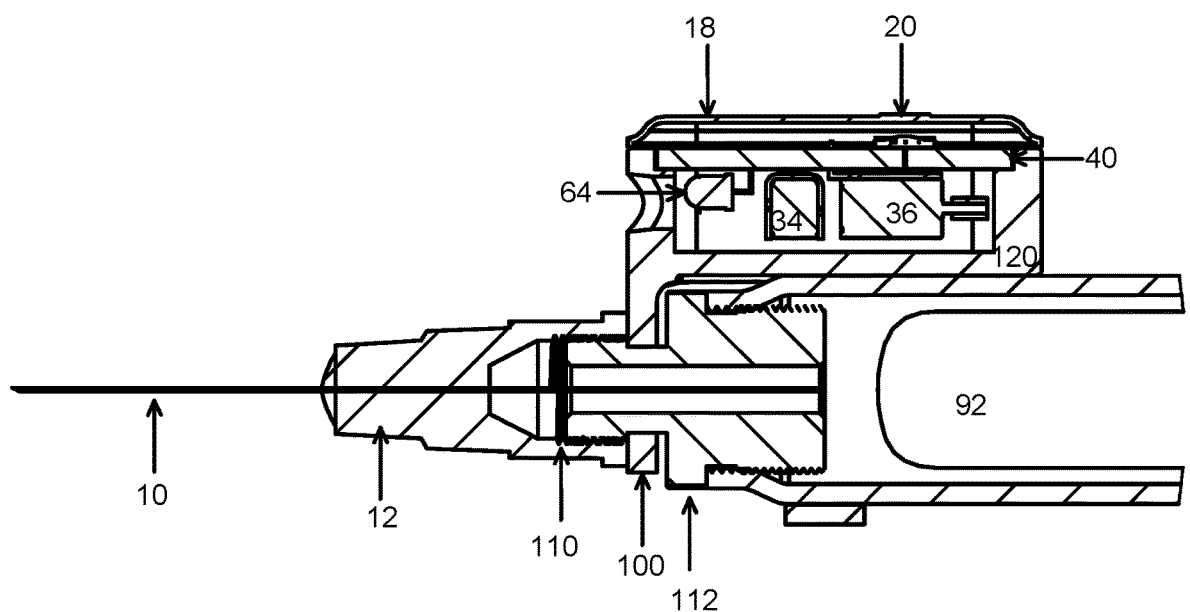

FIGS. 9 through 16 depict a reusable embodiment of the device that is installed upon a conventional dental anesthesia self-aspirating injection syringe. A conventional dental injection syringe is typically formed of metal and is reusable upon being autoclaved or chemically sterilized. The exposed components of the reusable embodiment must be composed of metal or other materials allowing it to be autoclaved or sterilized chemically. FIG. 9 depicts an angled top view of the reusable embodiment, while FIG. 10 depicts an exploded view of FIG. 9.

Thumb ring 9 is utilized by a user's thumb to control dispensing of anesthetic. Anesthetic is contained within piston 92. Barrel ring 94 secures the device onto the barrel of the self-aspirating syringe. Barrel ring 94 may be composed of metal. Adaptor 96 couples needle hub 12 to the self-aspirating syringe. Opening 66 allows LED light 64 (shown in FIG. 8) to focus light onto needle 10. Cover 18 may be removed from case 120 so that the vibrator motor components may be removed during autoclaving of the device. On/Off button 20 may be utilized to control vibration of needle 10.

FIG. 10 depicts the device separated from the self-aspirating syringe. Piston 92 may contain anesthetic. Adaptor 96 screws onto threaded tip 110. Tip ring 100 fits over threaded tip 110 and flush against the syringe adaptor 112 preventing the device from rotating or moving about the barrel of the self-aspirating syringe during use. Case 120, tip ring 100, and barrel ring 94 may be composed of metal that can be autoclaved.

A mid-sectional view of the device installed upon the barrel of a self-aspirating syringe. Needle 10 connects to piston 92 so that anesthetic may be released. Needle 10 traverses needle hub 12, which is threaded onto threaded tip 110 of the syringe. Tip ring 100 is securely fitted onto syringe adaptor 112. Case 120 is hollow to allow storage of battery 34, vibrator motor 36, and LED light 64. Cover 18 may be reversibly coupled onto case 120. On/Off button 20 manipulates vibrator motor 36. PCB 40 mechanically and electrically couples the vibrator motor components together.

FIG. 12 illustrates a side view of the reusable embodiment, while FIG. 13 illustrates the device of FIG. 12 with the vibrator motor components removed from case 120. Tip ring 100 and barrel ring 94 are formed onto case 120. Cover 18 fits securely onto case 120 via sealing edge 50 preventing fluids from entering motor cavity 122. On/Off switch 20 manipulates vibrator motor 36. Weight 80 is free to move within motor cavity 122. Battery 34 is secured via battery clip 76.

Figure 14:
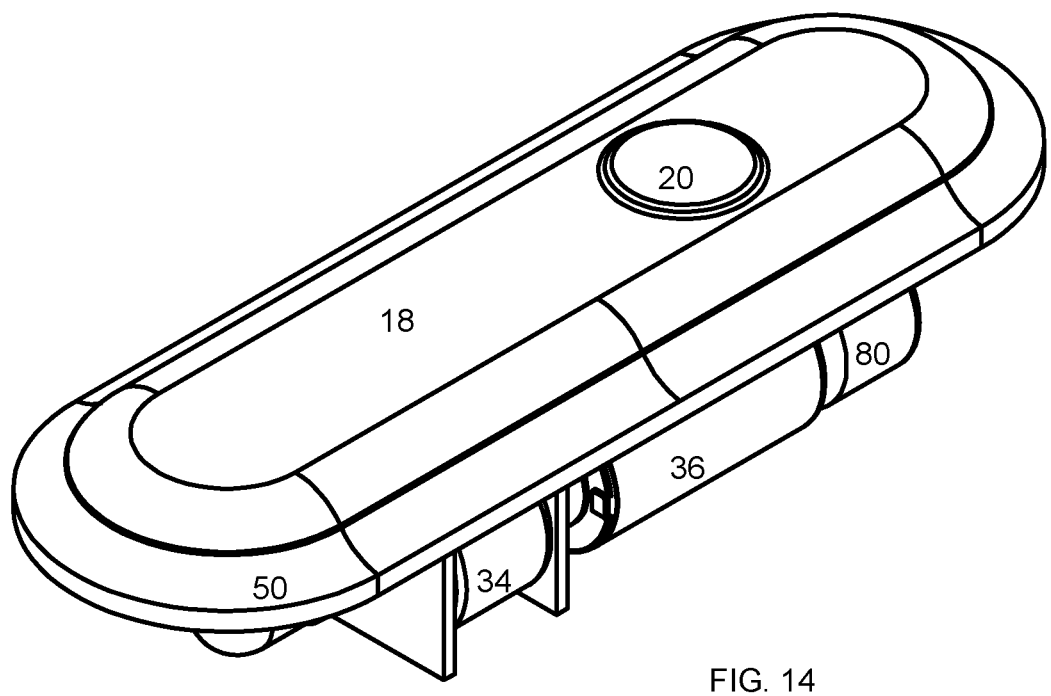
Figure 15:
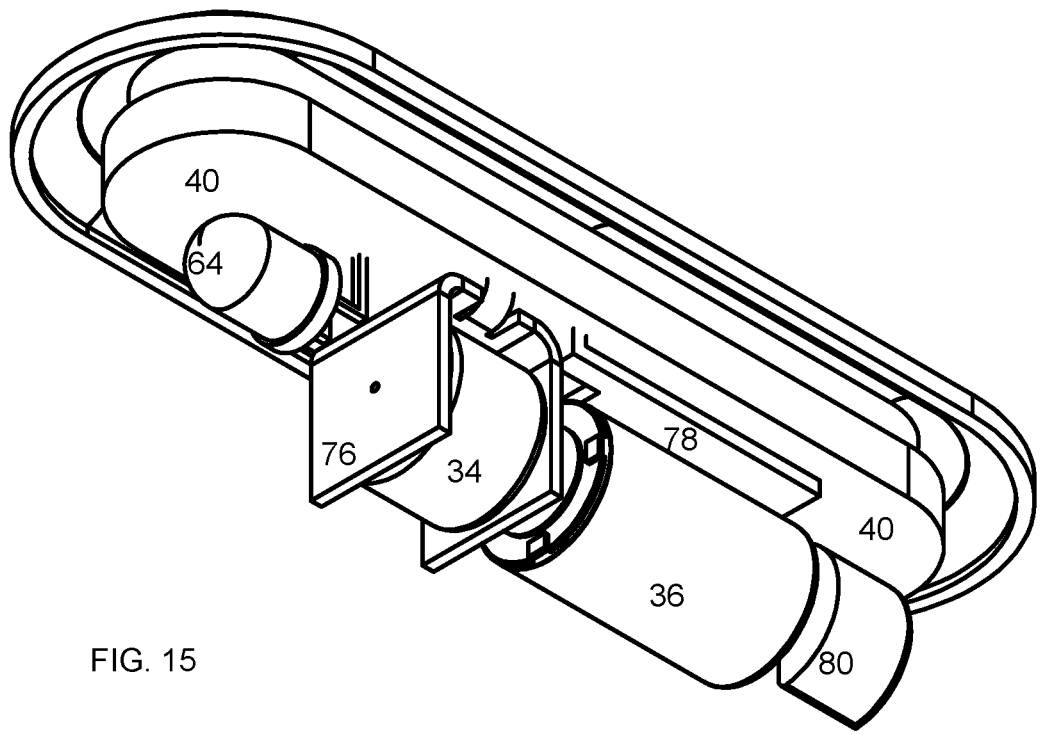

FIGS. 14 and 15 depict angled views of the vibrator motor components coupled to cover 18. In the reusable embodiment, cover 18 may be composed of metal. Sealing edge 50 is used to secure cover 18 onto case 122. Battery 34 is secured onto PCB 40 via battery clip 76. Vibrator motor 36 is secured onto PCB 40 via motor clip 78. LED light 64 is electrically and mechanically secured coupled to PCB 40. Weight 80 extends from vibrator motor 36.

Figure 16:
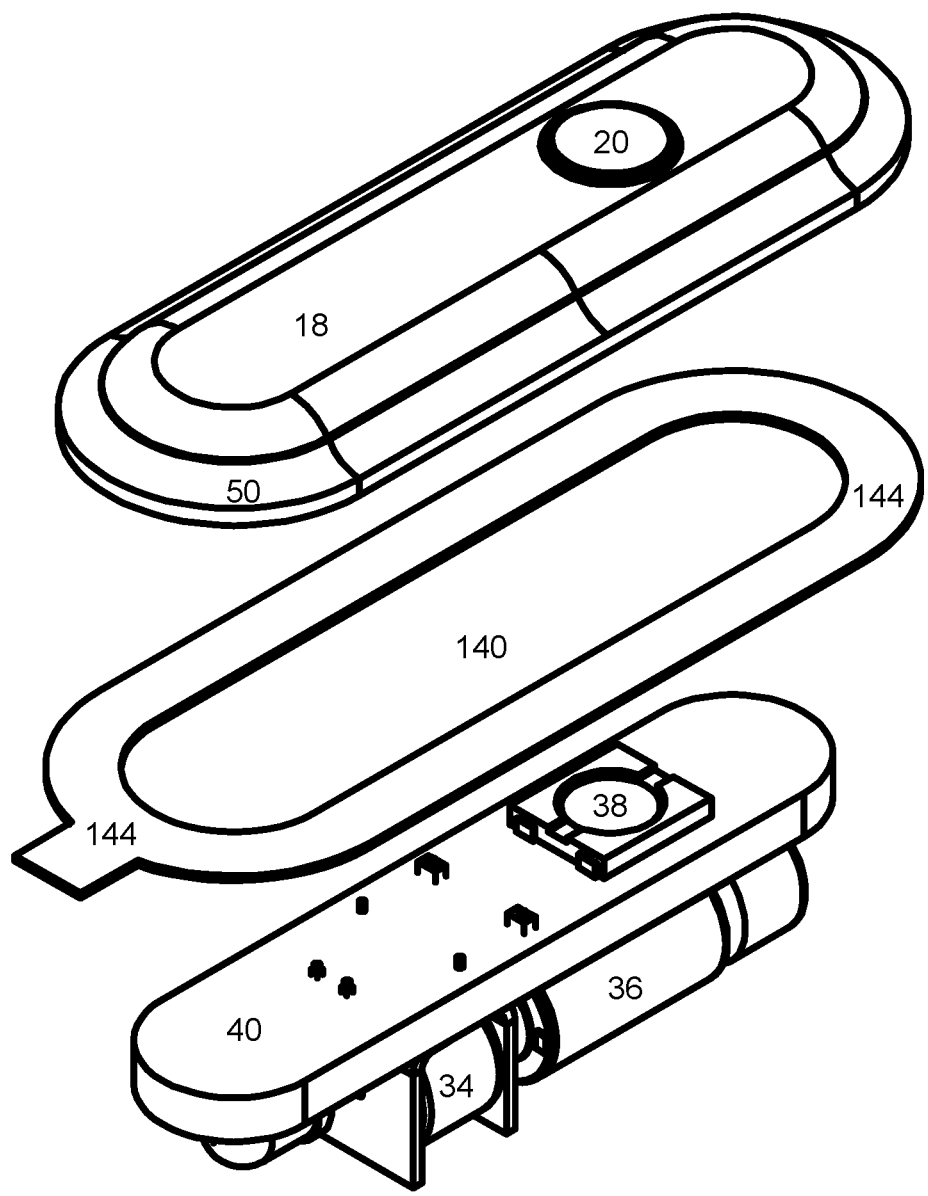

The vibrator motor components may be removed from motor cavity 122, and disconnected from cover 18 so that cover 18 and base 122 may be autoclaved or sterilized. FIG. 16 illustrates the disassembly of the vibrator motor components from cover 18. Adhesive strip 144 of membrane 140 may be positioned so that adhesive strip 144 adheres to sealing edge 50 of cover 18 providing a moisture barrier when cover 18 is attached to case 122. Membrane 140 may be composed of any material that serves as a waterproof barrier yet responsive enough to allow pressure from a user pressing upon On/Off switch 20 to be transmitted to electronic button 38. Membrane 140 protects PCB 40, battery 34, and vibrator motor 36 by preventing the entry of moisture into inner cavity 122. Membrane 140 may be disposable and replaced by a unused membrane 140 following autoclaving and/or sterilization of case 122 and cover 18.

I hereby claim:

1. An dental anesthetic device comprising:
   a needle to deliver anesthetic,
   a barrel to hold anesthetic, wherein the barrel couples to the needle via an adaptor, and
   a vibration device that reversibly couples to the adaptor via a metal ring and reversibly couples to the barrel via a metal ring,
      wherein the vibration device is positioned proximate to the needle,
      wherein the vibration device is fixed onto the adaptor so that it does not rotate about the adaptor, and
      wherein the vibration device is fixed onto the barrel so that it does not move along a length of the barrel.

2. The device of claim 1 further comprising a light source that projects light onto the needle.

3. The device of claim 1 further comprising a switch that allows a user to turn the vibration device on or off.

4. The device of claim 1 wherein the vibration device further comprises a battery, a DC micro motor, a button that allows a user to turn the micro motor off and on, and a printed circuit board that electrically connects the battery, the DC micro motor, and the button, wherein the printed circuit board mechanically supports the battery, the DC micro motor, and the button.

5. An autoclavable dental anesthetic device comprising:
   a needle to deliver anesthetic,
   a barrel to hold anesthetic, wherein the barrel couples to the needle via an adaptor,
   a metal case enclosing a vibration device, wherein the metal case reversibly couples to the adaptor via a metal ring and reversibly couples to the barrel via a metal ring,
      wherein the metal case is positioned proximate to the needle,
      wherein the metal case is fixed onto the adaptor so that it does not rotate about the adaptor, and
      wherein the metal device is fixed onto the barrel so that it does not move along a length of the barrel, and
   a vibration device comprising: a battery, a DC micro motor, a button that allows a user to turn the micro motor off and on, and a printed circuit board that electrically connects the battery, the DC micro motor, and the button, wherein the printed circuit board mechanically supports the battery, the DC micro motor, and the button.

* * * * *